United States Patent [19]

Akkara et al.

[11] Patent Number: 5,143,828

[45] Date of Patent: Sep. 1, 1992

[54] METHOD FOR SYNTHESIZING AN ENZYME-CATALYZED POLYMERIZED MONOLAYER

[75] Inventors: Joseph A. Akkara, Holliston; David L. Kaplan, Stow; Lynne A. Samuelson, West Newton, all of Mass.; Braja K. Mandal, Oak Park, Ill.; Sukant K. Tripathy, Acton; Ferdinando F. Bruno, Lawrence, both of Mass.; Kenneth A. Marx, Francestown, N.H.

[73] Assignees: The United States of America as represented by the Secretary of the Army, Washington, D.C.; University of Massachusetts Lowell, Lowell, Mass.

[21] Appl. No.: 815,213

[22] Filed: Dec. 31, 1991

[51] Int. Cl.$^5$ .......................... C12P 7/22; C12P 1/00; C12N 9/02; C12N 9/04
[52] U.S. Cl. .................................... 435/41; 435/128; 435/156; 435/189; 435/190; 435/191; 435/192; 435/310
[58] Field of Search ............... 435/41, 156, 189, 190, 435/191, 192, 128, 310

[56] References Cited

U.S. PATENT DOCUMENTS

| | | | |
|---|---|---|---|
| 4,309,453 | 1/1982 | Reiner et al. | 427/54.1 |
| 4,645,693 | 2/1987 | Roberts et al. | 427/402 |
| 4,715,986 | 12/1987 | Gruning et al. | 252/315.2 |
| 4,822,853 | 4/1989 | Uekita et al. | 528/125 |
| 4,830,952 | 5/1989 | Penner et al. | 430/287 |
| 4,907,038 | 3/1990 | Shigehara et al. | 428/338 |
| 4,910,293 | 3/1990 | Uekita et al. | 528/353 |
| 4,940,516 | 7/1990 | Wegmann et al. | 204/14.1 |
| 4,960,635 | 10/1990 | Erdelen et al. | 428/220 |
| 4,988,570 | 1/1991 | Ueikita | 428/411.1 |

OTHER PUBLICATIONS

J. A. Akkara et al., abstract entitled "Synthesis and Characterization of Polyphenols from Peroxidase-Catalyzed Reactions", presented at the International Conference on the New Science and Techniques for Biocatalysis, held Jun. 5-7, 1991 in Orlando, Fla., and published at that meeting by Enzyme and Microbial Technology, vol. 13, No. 6, Jun. 1991, p. 521.

F. Bruno et al., preprint entitled, "Enzyme Catalyzed 2-D Polymerization of Phenol Derivatives on a Lanqmuir-Blodgett Trough" Polymer Preprints, vol. 32 No. 1, Apr. 1991, pp. 232-233, Published by the Division of Polymer Chemistry, Inc., American Chemical Society, Washington, D.C.

Primary Examiner—Herbert J. Lilling
Attorney, Agent, or Firm—Richard J. Donahue

[57] ABSTRACT

A method for synthesizing enzyme-catalyzed polymers using the Langmuir-Blodgett technique. In one embodiment, the process comprises spreading one or more enzyme-polymerizable monomers on a water-miscible solvent. The monomers are sufficiently surface active that they align themselves on the air-solvent interface. Next, pressure is applied to the interface to form a monolayer made up of the monomers. An enzyme is then introduced into the solvent, causing polymerization of the monomers in the monolayer. The polymeric monolayers produced by the present method are easier to process and have reduced cross-linking and branching as compared to similar polymers produced in bulk by enzyme-catalyzed reactions.

13 Claims, 2 Drawing Sheets

METHOD FOR SYNTHESIZING AN ENZYME-CATALYZED POLYMERIZED MONOLAYER

The invention described herein may be manufactured, used and licensed by or for the Government for Governmental purposes without the payment to us of any royalty thereon.

BACKGROUND OF THE INVENTION

The present invention relates generally to the synthesis of enzyme-catalyzed polymers and more particularly to the synthesis of an enzyme-catalyzed, polymerized monolayer.

Highly conjugated, enzyme-catalyzed polymers have been found to possess desirable optical, electrical, and/or mechanical properties. Consequently, a need for producing such polymers clearly exists. Unfortunately, the methods currently in use for producing such polymers often result in polymers which cannot be processed easily into films, fibers, membranes, or other desirable structures. In addition, these same methods often result in polymers having a high degree of cross-linking and branching, which tends to disrupt the directionality of the electronic and/or optical properties of the polymers.

The Langmuir-Blodgett technique has been used for many years to form unpolymerized monolayer or monomolecular films. Generally speaking, the Langmuir-Blodgett technique involves filling an open basin with a liquid subphase typically comprising a quantity of water and/or a water-miscible solvent. A small number of molecules, each molecule typically having a hydrophilic head group and a hydrophobic tail, are then deposited at the air-subphase interface. The molecules orient themselves at the air-subphase interface so that the hydrophilic head groups are in contact with the subphase and the hydrophobic tails are projected into the air. Because only a small number of molecules are typically spread over the air-subphase interface, the molecules are initially separated far apart relative to one another. A movable barrier in the basin is then used to compress the air-subphase interface until the molecules disposed thereat arrange themselves in an ordered, two-dimensional lattice. This lattice, which takes the form of a monomolecular or monolayer film, is then typically removed from the trough and deposited on a desired substrate. Frequently, more than one monolayer is constructed in this manner, the monolayers being used to form a multi-layered laminate.

Because the molecules of a typical Langmuir-Blodgett film are not bonded together, but rather, are held in place by their lattice arrangement, many such films have poor mechanical stability and cannot be processed into useful structures. In an attempt to increase the mechanical stability of such films, efforts have recently been focused on various thermal, photochemical, and chemical catalytic means for polymerizing the constituent molecules of these monolayer films. One such known approach involves introducing a diacetylene functional group into the monolayer and then heating or irradiating the film so as to produce a polydiacetylene polymer. Another known approach involves using a vinyl functional group, instead of a diacetylene functional group, to produce a polyvinyl polymer.

SUMMARY OF THE INVENTION

It is an object of the present invention to provide a novel technique for synthesizing enzyme-catalyzed polymers.

It is another object of the present invention to provide a technique as described above which results in the production of highly resonant polymers which can be processed easily into fibers, films, membranes, and other similar structures.

It is still another object of the present invention to provide a technique as described above which results in the production of highly resonant polymers which have reduced cross-linking and branching as compared to similar enzyme-catalyzed polymers produced in bulk.

Additional objects, as well as features and advantages of the present invention, will be set forth in part in the description which follows, and in part will be obvious from the description or may be learned by practice of the invention. The objects, features, and advantages of the present invention may be realized and attained by means of the instrumentalities and combinations particularly pointed out in the appended claims.

The present invention is premised on the discovery that improved processability and functional properties are imparted to enzymatically synthesized polymers which are arranged in the ordered, two-dimensional, lattice structure of a monolayer. Monolayer formation may be achieved, for example, using the Langmuir-Blodgett technique.

Accordingly, to achieve the foregoing objects and in accordance with the purpose of the invention, as embodied and broadly described herein, a method for synthesizing an enzyme-catalyzed, polmerized monolayer comprises the steps of spreading one or more monomers over a solvent subphase having an air-subphase interface, said one or more monomers being capable of forming a monolayer at said air-subphase interface and being polymerizable with an enzyme system, compressing said air-subphase interface so as to form said monolayer comprising said one or more monomers, and polymerizing said one or more monomers with said enzyme system.

The present invention is also directed to the polymerized monolayers made in accordance with the above method and to laminates, fibers and other similar structures obtained from said polymerized monolayers.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawings wherein like reference numerals represent like parts.

DETAILED DESCRIPTION OF PREFERRED EMBODIMENTS

As discussed above, the present invention is directed to a new technique for synthesizing enzyme-catalyzed polymers. An important feature of this technique involves arranging the constituent monomers of the polymer in a monolayer film. This may be achieved, for example, using the Langmuir-Blodgett technique.

Figure 1:
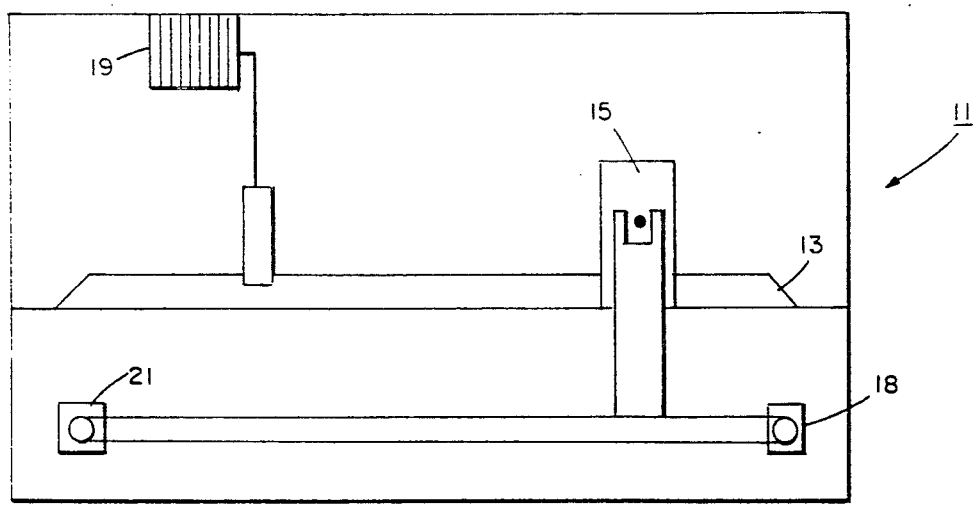
FIG. 1 is a schematic view of a conventional Langmuir trough, which may be used to practice the technique of the present invention.

Referring now to FIG. 1, there is illustrated a conventional Langmuir trough which may be used to practice the technique of the present invention, the Langmuir trough being represented generally by reference numeral 11.

As can be seen, trough 11 is used to hold a solvent subphase 13. The solvent subphase typically includes water and/or a water-miscible solution, the precise composition of the subphase being largely dependent on the nature of the monomer molecules and the polymerizing enzyme added thereto. Trough 11 also includes a pair of barriers 15 and 17, which are disposed in subphase 13. Barrier 15, which is mechanically coupled to a motor 18, is used to compress the air-subphase interface of the solvent against barrier 17 so as to form a monolayer at the interface. A pressure sensor 19, which is used to monitor pressure at the air-subphase interface, is mounted on barrier 17. Trough 11 also includes a position encoder 21, which is used to monitor the location of barrier 15 as it moves towards barrier 17. The readings obtained by sensor 19 and position encoder 21 may be used to generate a pressure isotherm.

Figure 2A:
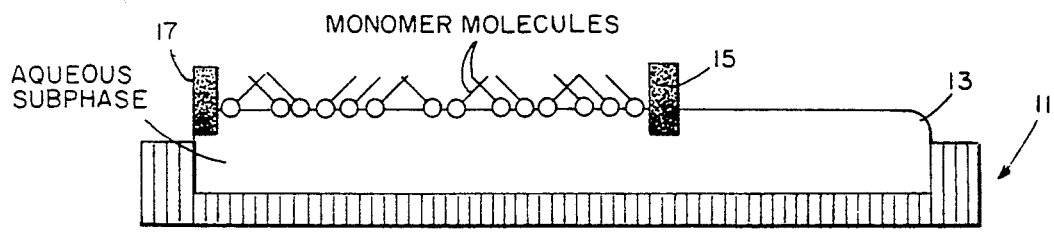
FIGS. 2(a) through 2(c) are schematic representations of one embodiment of a process for synthesizing an enzyme-catalyzed, polymerized monolayer in accordance with the teachings of the present invention.
Figure 2B:
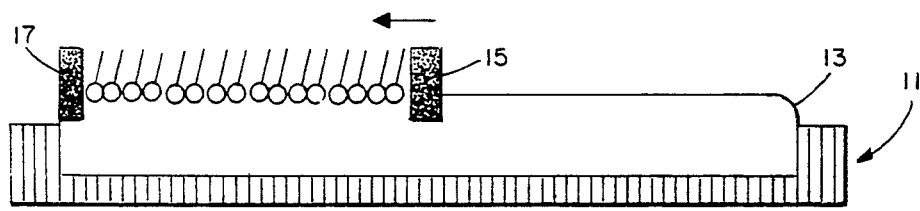
Figure 2C:
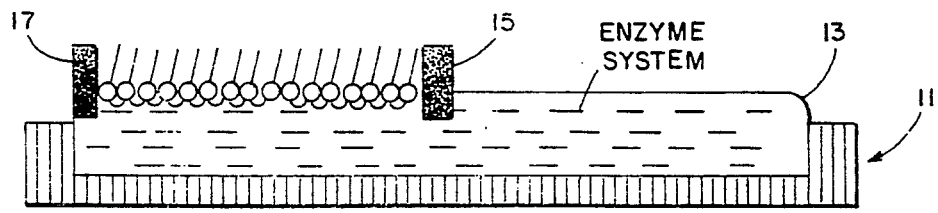

Referring now to FIGS. 2(a) through 2(c), the manner in which trough 11 may be used to make an enzyme-catalyzed, polymerized monolayer film in accordance with one embodiment of the present invention is shown schematically. As seen in FIG. 2(a), a plurality of monomer molecules are first spread on top of a water-miscible solvent subphase. Because the molecules include a hydrophilic head group and a hydrophobic tail, the molecules orient themselves at the air-subphase interface so that the head groups are in contact with the subphase and the tails are projected into the air. However, because only a comparatively fes molecules are dispersed over a relatively large air-subphase interface, there is no ordering of the molecules relative to one another. As seen in FIG. 2(b), however, as barrier 15 compresses the air-subphase interface, the molecules orient themselves into the lattice structure of a monolayer film. The molecules of this monolayer are then polymerized as seen in FIG. 2(c) by introducing into the subphase a suitable enzyme system, which typically includes an enzyme capable of catalyzing polymerization of the molecules and, if necessary, any substrates required by the enzyme for its catalytic activity. Once polymerized, the monolayer film may be removed from the subphase and processed into desired structures.

Notwithstanding the fact that, in the process described above, the enzyme system is added to the subphase after compression of the interface is completed, it should be understood that the enzyme system also may be added to the subphase before or during compression of the air-subphase interface, the salient feature of the process being that polymerization of the monomers takes place at the air-subphase interface.

As is apparent from the above description, the monomers of the present invention must be capable of being polymerized by enzymes. Research conducted in bulk has revealed numerous enzyme-polymerizable monomers. The following articles, which are incorporated herein by reference, describe many such enzyme-polymerizable monomers: I. Yamazaky et al., *Oxidases and Related Redox Systems*, Vol. 1, pp. 407, University Park Press (1971); J. Dordick et al., *Biotechnol. Bioeng.*, Vol. 30, pp. 31 (1987); and B. C. Saunders et al., *Peroxidase—The Properties and Uses of a Versatile Enzyme and of Some Related Catalysis*, Butterworth, Washington DC, pp. 28-34 (1964). In addition, in *Synthesis and Characterization of Polymers Produced by Horseradish Peroxidase in Dioxane* by J. Akkara et al., J. Polymer Sci., in press, 1991, a number of monomers which have been polymerized in bulk by horseradish peroxidase are disclosed. These monomers, which are set forth below in the Table, were used to make both homopolymers and copolymers in a dioxane solvent buffer mixture (85:15) at pH values of 5.6, 7.0, and 7.5. Copolymers were prepared from a mixture of substituted phenolic and aromatic amine monomers.

| Phenolic Functional Gp. | Amine Functional Gp. | Mixed Functional Gp. |
|---|---|---|
| Phenol | Aniline | 8-Hydroxyquinoline |
| Anisole | Benzidine | Isoquinoline |
| Cresols(o, m & p) | 3-Phenylenediamine | Tyrosine |
| 1,2-Benzenediol | Phenylethylamine | 4-Phenylazo phenol |
| 2-Hydroxybenzylalcohol | | 4-(2-Pyridylazo)resorcinol |
| 2-Methoxyphenol | | |
| 3-Methoxyphenol | | 2-Methyl 8-quinolinol |
| 3,4-Dimethylphenol | | 4-Amino m-cresol |
| 4-Phenylphenol | | |
| 3-Phenylphenol | | |
| 4-Phenoxyphenol | | |
| 3-(3-Phenoxyphenoxy)phenol | | |
| Diethylstilbesterol | | |
| 1-Hydroxynaphthalene | | |
| 2-Hydroxynaphthalene | | |
| 1,3-Dihydroxynaphthalene | | |
| 1,5-Dihydroxynaphthalene | | |
| Hematein | | |

Other examples of enzyme-polymerizable monomers include lipid and amino acid or peptide monomers, which may be polymerized with lipases and proteases, respectively.

It is also undoubtedly apparent from the foregoing description that the monomers of the present invention must be capable of forming a monolayer at the air-subphase interface of the solvent subphase. Where the subphase is water-miscible, this is typically achieved by selecting monomers that are sufficiently surface active that they position themselves at the air-subphase interface. Unfortunately, in some cases, the organization of monomers at the interface is not consonant with the geometry sought after by the enzyme for polymerization. In these cases, it is often necessary to design the composition of the interface, e.g. by altering the ratio of monomers at the interface or by selecting one or more monomers of varying hydrophobicities, so that the arrangement of monomers at the interface is more acceptable to the preferences of the enzyme. For example, it has been found that horseradish peroxidase prefers an arrangement of monomers at the interface wherein one type of monomer (e.g. a long-chain alkyl phenol) is aligned at the interface while the other type of monomer (e.g. underivatized phenol, an aromatic amine, etc.) is partitioned to varying degrees between the subphase and the air-subphase interface.

The rate and the type of polymerized monolayer synthesized may be modified by altering the composition of the suphase with respect to pH, ionic strength, buffer, and organic solvent concentration. Additionally, the rate of polymerization may be regulated by altering the temperature of the subphase during the polymerization reaction.

It should be understood that, where the monolayer comprises two or more different monomers, these monomers may be distributed either uniformally so as to form a monophasic monolayer or non-uniformally so as to form a bi- or polyphasic monolayer.

Another embodiment of the present invention involves providing a monolayer of one or more monomers which will not polymerize unless simultaneously exposed to both light of a certain wavelength and the appropriate enzyme system. The advantage to such a monolayer is that polymerization can be effectively limited to specific, localized areas by limiting the amount of monolayer that is irradiated.

Another manner in which polymerization may be confined to specific portions of the monolayer is to provide a polyphasic monolayer which includes, for example, three or more different monomer species which are selected so that polymerization will occur only where a subset of the three or more different monomer species are located in proximity to one another.

The following examples further illustrate preferred embodiments of the present invention. The examples should in no way be taken as limiting, but rather, should be considered to be illustrative of the various features of the present invention.

EXAMPLE 1

Figure 3:
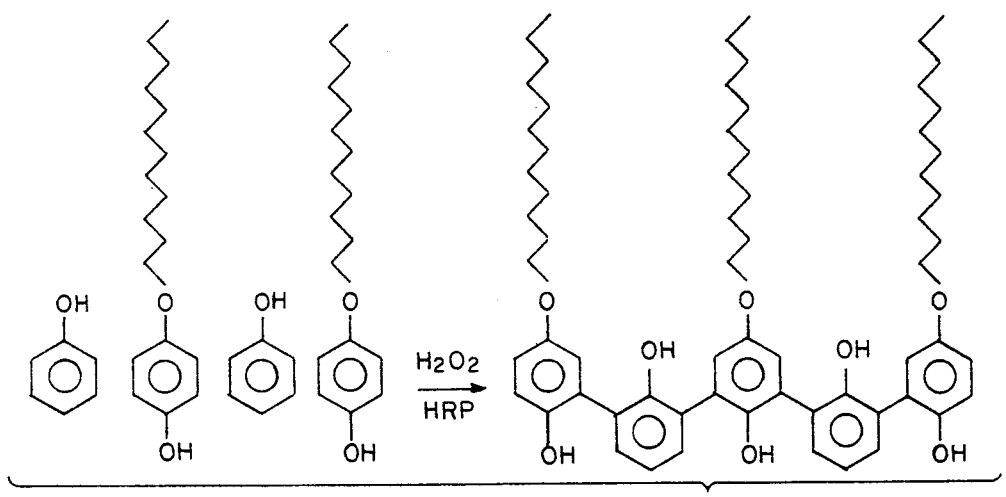
FIG. 3 is a proposed representation of the polymerization reaction that takes place in Example 1.

A Langmuir film trough equipped with a constant temperature bath set at 20.0 degrees C. was filled with two liters of a buffer solution (50-200 mM, pH=5.6-7.5) in MilliQ water into which 12.0-25.0 mg of horseradish peroxidase per liter of solution had already been introduced. A chloroform solution of 4-tetradecyloxyphenol (1-2 mg/ml) and phenol in a 1:1 to 1:500 ratio, respectively, was spread on the air-water interface. The mixed spreading solutions were dispersed at the air-water interface and then slowly compressed at speeds of about 1.0 $A^2$ $mol^{-1}$ $min^{-1}$ to a surface pressure of 5 mN/m prior to deposition. After reaching this pressure (approximately 15-20 minutes after depositing the monomers), a 0.30 ml aliquot of hydrogen peroxide (30% in water) was injected under the monomers to initiate polymerization. The system was left to react for 8-15 hours. FIG. 3 depicts the polymerization reaction believed to occur.

EXAMPLE 2

Figure 4:
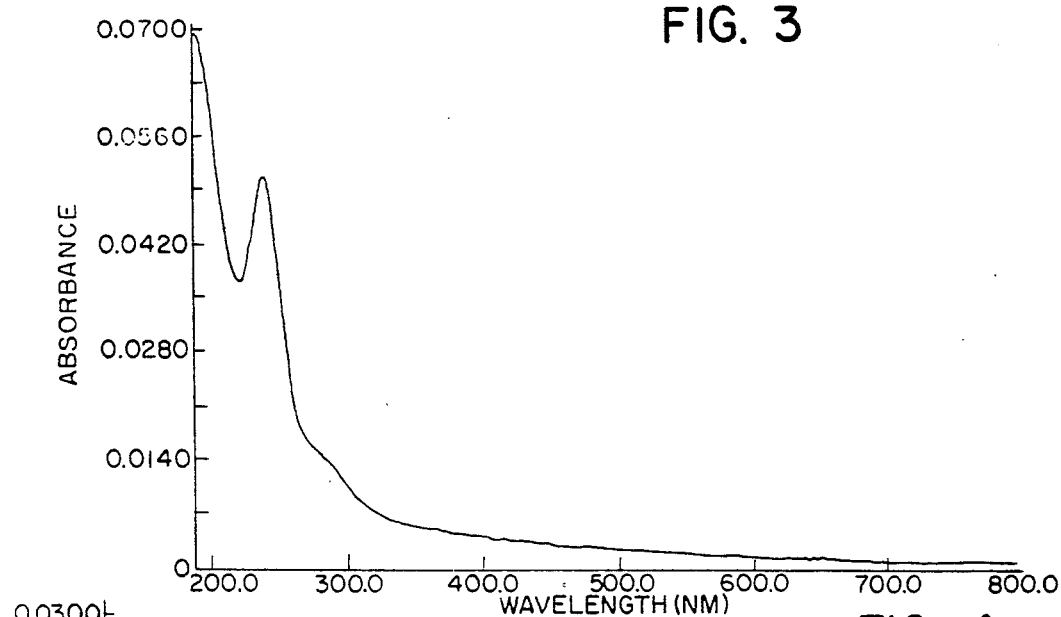
FIG. 4 is a UV-Vis spectrum for the polymerized film obtained in Example 2.
Figure 5:
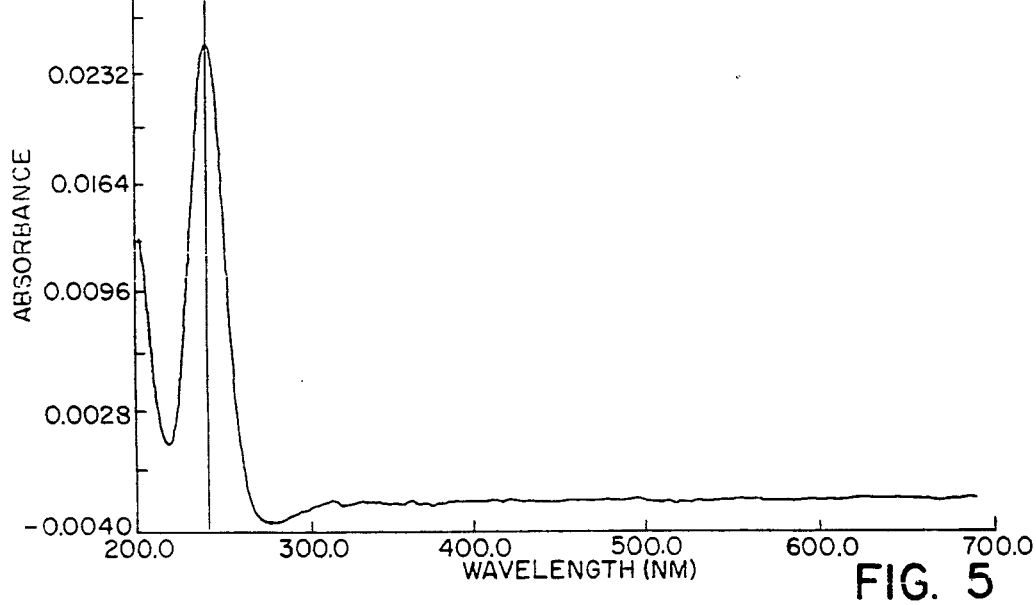
FIG. 5 is a UV-Vis spectrum for a solution of the C14PP monomer used in Example 1.

The polymerized monolayer formed in Example 1 was transferred to quartz slides by a sequential process resulting in the stacking of ten monolayers. This product was then measured by UV/Vis spectroscopy using a Perkin Elmer Lambda-9 UV-Vis-near IR spectrophotometer. The result of this measurement is the spectrum shown in FIG. 4. As one can see, the spectrum includes a large, broad absorption tail in the visible (from 300-600 nm) and near IR, which is not present in a similar spectrum obtained from the monomer 4-tetradecyloxyphenol (see FIG. 5). The absorption band in FIG. 4 is indicative of the presence of an extended degree of conjugation in the polymerized monolayer.

EXAMPLE 3

The experiment was performed substantially as set forth in Example 1 except that the ratio of 4-tetradecyloxyphenol (hereinafter referred to as C14PP) to phenol was 1:1. Results similar to those set forth in Example 2 were obtained.

EXAMPLE 4

The experiment was performed substantially as set forth in Example 3 except that laccase was used instead of horseradish peroxidase to polymerize the monomers. (Consequently, hydrogen peroxide was not required for polymerization.) To initiate polymerization, laccase was injected into the subphase. Results similar to those set forth in Example 2 were obtained.

EXAMPLE 5

The experiment was performed substantially as set forth in Example 3 except that ethylphenol was used instead of phenol. Results similar to those set forth in Example 2 were obtained.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for synthesizing an enzyme-catalyzed, polymerized monolayer comprising the steps of:
    a) spreading at least one or more monomers selected from the group consisting of a phenol an an aromatic amine over a water-miscible solvent subphase having an air-subphase interface, said one or more monomers being capable of forming a monolayer at said air-subphase interface and said one or more monomers being polymerizable with an oxidase enzyme system by introducing the enzyme into the subphase;
    b) compressing said air-subphase interface so as to form a monolayer comprising said one or more monomers whereby there is an arrangement of monomers at the interface wherein at least one monomer is aligned at the interface while at least one other monomer is partitioned to varying degrees between the subphase and air-subphase interface; and
    c) polymerizing said monomers to form a copolymerized monolayer with said enzyme system.

2. The method as claimed in claim 1 wherein said polymerizing step is initiated during said compressing step.

3. The method as claimed in claim 1 wherein said polymerizing step is initiated after said compressing step.

4. The method as claimed in claim 1 wherein said polymerizing step is initiated before said compressing step.

5. The method as claimed in claim 1 wherein said enzyme system is selected from the group consisting of laccase and horseradish peroxidase and hydrogen peroxide.

6. The method as claimed in claim 5 wherein said enzyme system comprises horseradish peroxidase and hydrogen peroxide.

7. The method as claimed in claim 6 wherein said one or more monomers comprises an alkyl-substituted phenol and a compound selected from the group consisting of phenol and ethylphenol.

8. The method as claimed in claim 7 wherein said alkyl-substituted phenol is 4-tetradecyloxyphenol.

9. The method as claimed in claim 8 wherein said compound selected from the group consisting of phenol and ethylphenol is phenol.

10. The method as claimed in claim 8 wherein said compound selected from the group consisting of phenol and ethylphenol is ethylphenol.

11. The method as claimed in claim 6 wherein said one or more monomers comprise one or more alkyl-substituted phenols and/or one or more aromatic amines.

12. The method as claimed in claim 5 wherein said enzyme system comprises laccase.

13. The method as claimed in claim 5 wherein said one or more monomers comprise phenol and one or more alkyl-substituted phenols.

* * * * *